United States Patent [19]

Picciola et al.

[11] Patent Number: 4,826,975

[45] Date of Patent: May 2, 1989

[54] FUSED CYCLOALIPHATIC AMINOALCOHOLS

[75] Inventors: Giampaolo Picciola, Milan; Mario Riva, Monza; Franco Ravenna, Milan; Piergiorgio Gentili, Treviglio, all of Italy

[73] Assignee: Maggioni-Winthrop S.P.A., Milan, Italy

[21] Appl. No.: 940,089

[22] Filed: Dec. 10, 1986

[30] Foreign Application Priority Data

Jun. 25, 1986 [GB] United Kingdom ............... 8615560

[51] Int. Cl.$^4$ .................. C07C 93/14; C07D 295/08; C07D 295/18; C07D 211/58
[52] U.S. Cl. .................. 544/391; 544/365; 544/378; 544/379; 544/392; 544/395; 544/398; 546/199; 546/200; 546/201; 546/206; 546/197
[58] Field of Search ............... 546/199, 198, 197, 200, 546/201, 206; 544/362, 391, 365, 379, 392, 395, 398, 378

[56] References Cited

U.S. PATENT DOCUMENTS

| | | | |
|---|---|---|---|
| 2,549,685 | 4/1951 | Heinzelmann | 564/391 |
| 4,022,791 | 5/1977 | Welch | 546/199 X |
| 4,533,745 | 8/1985 | McClure | 560/28 |

FOREIGN PATENT DOCUMENTS

| | | |
|---|---|---|
| 0000395 | 1/1979 | European Pat. Off. . |
| 2323388 | 4/1977 | France . |
| 50-151853 | 12/1975 | Japan . |

OTHER PUBLICATIONS

Chem. Ab. 89 (13), 108770, 1978.
Chem. Ab. 84, 105281, 1976.
Chem. Ab. 71(19), 91148, 1969.
Chem. Ab. 71, 61032, 1969.
Chem. Ab. 85(9), 62844, 1976.
Hagishita, S. et al., *J. Chem. Soc., Perkin Trans. 1*, 1984, (8), 1644–1669.
Rimek, H. et al., *Justus Liebigs Ann. Chem.* 1969, 726, 25–29.
Journal of Chemical Society C. 1967 (U.S.), R. I. Thrift: "Derivatives of 2-aminotetralin", pp. 288–293.
European Journal of Medicinal Chemistry, vol. 18, No. 3, 1983 Chatenay-Malabry (FR) J. G. Cannon: "Demi-rigid Ketone Congeners of Catecholemines", pp. 291–292.
Chemical Abstracts, vol. 85, No. 9, Aug. 30, 1976, Columbus, Ohio (U.S) see p. 542, abstract 62844s & JP, A, 75151853 (Takeda Chemical Industries, Ltd), Dec. 6, 1975.

*Primary Examiner*—Teddy S. Gron
*Assistant Examiner*—Virginia B. Caress
*Attorney, Agent, or Firm*—Oblon, Fisher, Spivak, McClelland & Maier

[57] ABSTRACT

The invention is concerned with fused cycloaliphatic aminoalcohols having pharmacological activity as antihypertensive, platelet aggregation inhibiting, hypolipemic, antianoxic and spasmolytic activity. The compounds have the generic formula

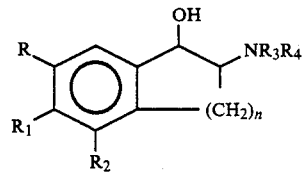

in which the symbol n is an integer selected from 1 to 2, the compounds pertaining therefore to the indanol and tetralol series.

7 Claims, No Drawings

FUSED CYCLOALIPHATIC AMINOALCOHOLS

This invention is concerned with new pharmacologically active compounds. More particularly, the compounds with which this invention is concerned are fused cycloaliphatic aminoalcohols of the formula:

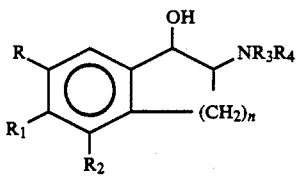

wherein n represents an integer selected from 1 and 2;

R, $R_1$ and $R_2$ represents hydrogen or a lower alkoxy group, with the proviso that at least two alkoxy groups are present, or two adjacent radicals selected from $R+R_1$ and $R_1+R_2$ represent an alkylenedioxy group, $R_3$ represents hydrogen and $R_4$ represents an alkyl group; or alternatively $R_3$ and $R_4$ taken together represent a divalent group selected from

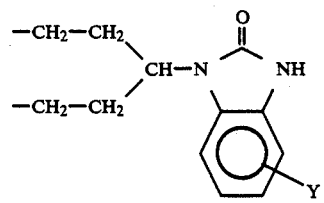 (a)

wherein Y represent hydrogen or halogen;

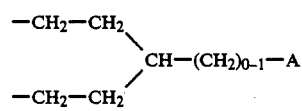 (b)

wherein A is a group selected from

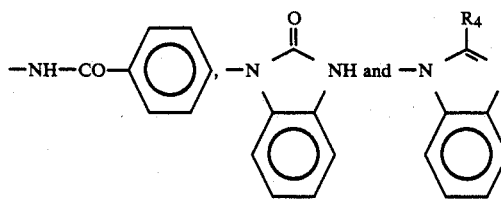

$R_4$ represents a lower alkyl group;

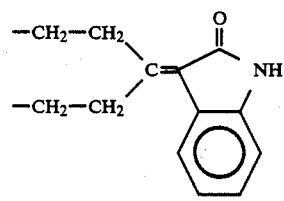 (c)

and

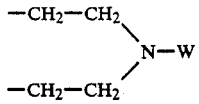 (d)

wherein W represents hydrogen, phenyl, alkoxyphenyl, methylphenyl, 2-furoyl, nicotinoyl radical or a radical $$-CO-CH=CH-Z$$

in which Z represents 2-thienyl or phenyl optionally substituted with 1-3 halogen or alkoxy groups: and their salts with inorganic acids, organic acids, cationic exchange resins and complexes with cyclodextrins.

As apparent to all those skilled in organic chemistry, the compounds, having two structural asymmetry centers, may exist both in the cis and trans configuration.

In most cases, by the manufacturing process which will be hereinafter described, a mixture of the two steric isomers is obtained, and an appropriate separation may occasionally be necessary. In other instances, however, formation of one single isomer is so prevailing as to approach 100 percent, and a separation is not required unless the product is desired in an analytically pure condition for purposes of study.

The configuration of the cis and trans isomers of the structure

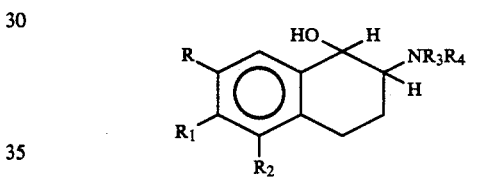

was assigned through $^1$H NMR (Nuclear Magnetic Resonance) spectra by determining the characteristic coupling constants ($J_{C-1,C-2}$) of several compounds. Said spectra show $C_1$-H as doublet with J=9.7–10.23 Hz in the trans derivatives and J=2.5–3.5 in the cis derivatives.

In the series of compounds of the structure

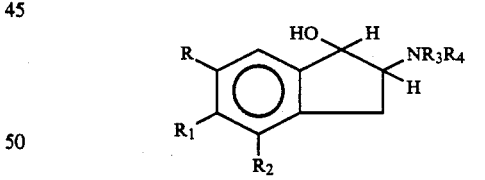

the configuration was assigned using the NOE (Nuclear Overhauser Effect). (J. H. Noggle and R. E. Schirmer, the Nuclear Overhauser Effect, Academic Press, London, 1971). Actually, the simple determination of the coupling constants through $^1$H NMR is not indicative, the differences between them being very small.

In addition to the NOE, the cis-trans configuration was also confirmed using the IR spectroscopy (H. J. Rimek et al. Liebigs Ann. Chem. 726, 25–29, 1969). The spectra of the individual isomers were registered at different concentrations using methylene dichloride as the solvent. It is well known that only the cis series forms intramolecular hydrogen bonds. In the present instance therefore, the intensity ratio between the free hydroxyl band and that of the bound hydroxyl remains constant by progressive dilution, while in the trans series that ratio markedly changes in favor of the free hydroxyl band.

The chemical process for the preparation of the invention compounds consists in contacting a bromo ketone of the partial formula IV with a secondary amine to give the amino ketone of the partial formula V.

The amino ketone is then hydrogenated to give the desired amino alcohol

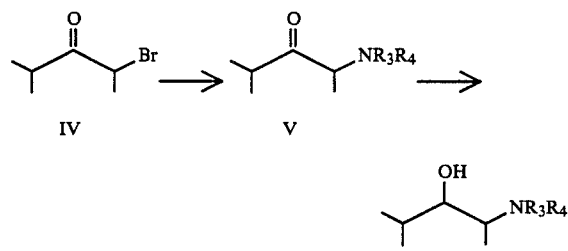

Depending on the circumstances, the amino ketone V may be isolated from the reaction mixture before it is hydrogenated. On the other hand, if the intermediate V show a low degree of stability, it is preferable to hydrogenate it directly in the reaction mixture in which it is formed by reaction of the bromo ketone with the secondary amine.

The first step of the process is carried out in the presence of a proton acceptor, such as an alkali metal or earth alkali carbonate or bicarbonate or a tertiary amine.

In some instances, an excess over the molecular amount of the same secondary amine which is being contacted with the bromo ketone may be used with satisfactory results. Usually this first step is carried out in an inert solvent such as a lower alkanol, for instance methanol or ethanol, or a ketone, such as a di-lower alkyl ketone, for instance acetone or methyl ethyl ketone. It is immaterial whether the amine is added to the bromo ketone, both or only one of them being dissolved in the solvent, or vice versa the bromo ketone is added to the amine, still both in solution or only one of them. The appropriate way of conducting the first step will be selected considering the properties of the reactants and their reactivity. The reaction temperature is also adjusted depending of the reactivity of the two reactants, although normally the boiling temperature of the solvent is generally preferred.

The second step of the process, i.e. the hydrogenation, may be carried out by any conventional hydrogenation procedure apt to convert a keto into a hydroxy group; However, we have found that the hydrogenation is best performed by using a metal hydride, preferably a double hydride, such as NaBH$_4$, LiAlH$_4$ etc., by conventional procedures in a solvent inert to the hydrogenation reaction, which in the case of NaBH$_4$ may be water, or a lower alkanol, such as methanol or ethanol, both in the presence of various amounts of water or under anhydrous condition; or alternatively, when for instance LiAlH$_4$ in used, the solvent may be diethyl ether, tetrahydrofuran and the like, at a temperature which may range from 0°–5° C. to the boiling temperature of the selected solvent.

When the intermediate is not isolated from the reaction mixture of the first reaction step, and depending on the nature of the selected hydrogenating agent, this may added directly to the intermediate reaction mixture either in the form of a solution in an appropriate solvent not interfering with the hydrogenation, and the solution of the hydrogenating agent is added while maintaining the mixture at the reflux temperature or at a lower temperature which may be found more convenient depending on the observed reaction rate; or the hydrogenating agent may be added at portions or by dropping its solution in an appropriate solvent while maintaining the reaction mixture at 0°–5° C. until the addition is complete, then heating the mixture to reflux until the reaction is complete.

Obviously the skilled chemist will select the procedure appropriate to the nature of the hydrogenating agent and the substrate and the reactant used.

An alternative process for preparing the invention compounds consists in reacting an amino alochol of the partial formula VI with an aldehyde of the partial formula VII at a temperature between about 0° C. and 20° C. in a solvent, preferably in a lower alkanol such

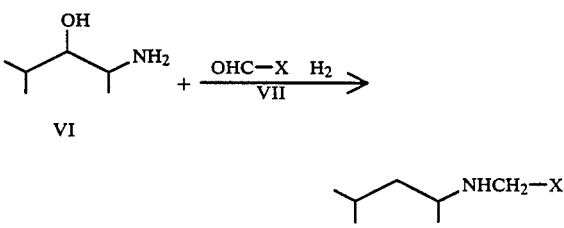

as methanol er ethanol, while adding at portions to the reaction mixture a hydrogenating agent preferably selected from metal hydrides or double hydrides or double cyano hydrides, such as sodium boron cyano hydride or lithium boron cyano hydride, these latter hydrogenating agents being preferred.

When the addition of the hydrogenation agent is terminated, the mixture is allowed to arrive slowly to the room temperature in order to complete the reaction.

It is apparent to those having knowledge of organic chemistry that the last described method of preparation is convenient when the symbol X in the partial formula VII above represents a linear or branched alkyl radical.

Alternatively, the hydrogenation may be carried out by using conventional procedures such as hydrogen in the presence of a catalyst.

The compounds of this invention show anti-hypertensive, platelet aggregation inhibiting, hypolipemic, antianoxic, spasmolytic, antithrombotic and Ca++ antagonizing activity.

The anti-hypertensive activity was tested on groups of 5 SH rats (spontaneously hypertensive rats) and 5 DOCA rats (deoxycorticosterone acetate and sodium chloride loaded rats) weighing 200±10 g, fasting from 18 hrs and treated orally with the invention compounds suspended in 0.5% gum arabic.

Changes in blood pressure (mm Hg) before (T=O) and after treatment (2, 4 and 6 hrs) were measured according to the method of tail artery plethysmography reported in "Spontaneously hypertensive rats (SHR), guidelines for breeding, care and use", SHR Conference, 1976, page 11.

The heart rate was also treated (BP Recorder No. 8006 supplied by Basile, Comerio, Italy). The arterial pressure before the treatment was 210±10 mmHg in SHR and 200±10 in DOCA rats.

Table 1 shows that the test compounds are endowed with good anti-hypertensive activity.

The peak effect was noted 2-4 hrs after the treatment and the duration of the effect was more than 6 hrs: in this period no remarkable increase of heart rate was registered. Some of the compounds were tested on SH rats at the dosis of 1 and/or 5 mg/kg and their activity appeared to be dose-dependent. For instance, administration of 5 mg/kg p.o. of MG 28401, M 28427 and MG 38007 causes a pressure decrease of 37.6, 26.2 and 20 mm Hg respectively. Administration of 1 mg/kg p.o. of MG 28427 causes a pressure decrease of 17.4 mm Hg.

Under the same conditions Tibalosine was poorly active at the dosis of 5 mg/kg p.o. (pressure decrease 13 mm Hg).

TABLE 1

| Compound | Max. changes in systolic pressure (mmHg) Dose tested = 15 mg/kg po | |
|---|---|---|
| | SHR | DOCA rats |
| MG 38005 | −42 | −27 |
| MG 38007 | −61.4 | −37.4 |
| MG 38019 | −56 | −23 |
| MG 28401 | −67 | −40.2 |
| MG 28427 | −47 | −41.2 |
| MG 38060 | −47 | −25.5 |
| MG 38112 | −35 | −19 |
| MG 38122 | −41.9 | −28 |
| Tibalosine | −67.0 | — |
| Urapidil | −72.4 | — |

To test the antagonism against phenylephrine (PHE) induced hypertension, male rats CrI:CD (SD)BR was anesthesized with urethane, 1 g/kg, i.p.

TABLE 2

| Compound | $DP_{50}$ mg/kg po | Conf. limits (P = 0.05) |
|---|---|---|
| MG 38007 | 10.0 | 7.6-13.1 |
| MG 28401 | 3.5 | 2.47-4.96 |
| MG 38028 | 0.73 | 0.47-1.12 |
| MG 38041 | 0.31 | 0.21-0.46 |
| MG 38060 | 1.28 | 0.99-1.65 |
| MG 38100 | 8.5 | 6.07-11.9 |
| MG 38112 | 4.4 | 3.4-5.7 |
| MG 38107 | 2.45 | 1.79-3.34 |
| MG 38119 | 4.4 | 3.31-5.84 |
| MG 38121 | 2.75 | 2.25-3.35 |
| MG 16456 | 1.85 | 1.39-2.85 |
| Prazosin | 0.70 | 0.59-0.83 |
| Tibalosine | 5.5 | 3.36-8.99 |
| Phentolamine | 8.0 | 6.3-10.15 |

The receptor binding assay for the inhibition of $^3H$-Prazosin, $^3H$-clonidine and $^3H$-spiperone binding to rat brain membrane was carried out according to Greenberg et al., Life Sci. 19, 69, 1976, and U'Prichard et al., Molec. Pharmacol. 13, 454, 1977.

Data for the tested compounds are reported in Table 3 where the 50% inhibiting concentrations ($IC_{50}$) of Tibalosine and Urapidil are also given. The invention compounds show a good affinity toward alpha$_1$-adrenergic receptors, comparable with or higher than the two comparison substances, and poor or no affinity toward alpha$_2$-adrenergic receptors.

A moderate affinity toward serotoninergic $_2$(5-HT$_2$) receptors is displayed by MG 38007 MG 28401.

TABLE 3

| Compound | Concentration (M) | % Inhibition of the specific binding | | |
|---|---|---|---|---|
| | | $^3H$—Prazosin ($\alpha_1$) | $^3H$—Clonidine ($\alpha_2$) | $^3H$—Spiperone (5-HI$_2$) |
| MG 38007 | $5.4 \times 10^{-7}$ | 75 | 3.5 | 49 |
| | $5.4 \times 10^{-6}$ | 96 | 32.5 | 93 |
| MG 38019 | $5.4 \times 10^{-7}$ | 35.5 | 0 | -10 |
| | $5.4 \times 10^{-6}$ | 82 | 6.7 | 33 |
| MG 28401 | $5.4 \times 10^{-7}$ | 54.5 | 0 | 41 |
| | $5.4 \times 10^{-6}$ | 92 | 0 | 81 |
| Tibalosine | $IC_{50}$ (a) | $4 \times 10^{-7}$ | $1 \times 10^{-3}$ | — |
| Uranidil | $IC_{50}$ (b) | $8 \times 10^{-7}$ | $1.4 \times 10^{-5}$ | — |

(a) Qlan J. Q. et al. - Arch. int. Pharmacodyn. 266, 264: 1983
(b) van Zwieten P. A. et al. - Arch. int. Pharmacodyn. 376, 180: 1985

PHE was administered cumulatively and dose-response curves were obtained (controls). Dose-response curves were similarly obtained after administration of the test drugs (1 mg/kg i.v.). From the two curves the PHE dosis causing a 50 mm Hg increase of the arterial pressure was calculated. The PHE dosis was about 3 times, in comparison with the controls, after administration of MG 28401 and MG 28427, and about 9 times after MG 38007, MG 38060 and 38041.

The protection against toxic adrenaline doses was tested as follows. Groups of 10-20 male mice CrI:CD 1(CR) BR were treated orally with carrier (controls) and with various doses of the compounds. After 2 hrs 14.5 mg/kg of 1-adrenaline was administered intraperitoneally and mortality was recorded after 24 hrs; in controls mortality was 100%. From log-dose-% protection curves the 50% protective doses were calculated (Litchfield et al., J. Pharmacol. Exp. Ther. 96, 99, 1949).

Table 2 gives the results obtained with some of the compounds as compared with known drugs.

The effect on platelet aggregation was tested ex vivo according to the method of Minsker, (J. Pharmacol. Exp. Ther. 210, 37, 1979) slightly modified. Groups of 3 rats (280-350 g) were treated orally with vehicle (controls) and compounds (0.15 mM/kg). Blood was collected and pooled from rats of each group 1 hr after treatment and the platelet rich plasma (PRP) was separated by centrifugation.

Platelet aggregation was stimulated with collagen (2-4-mcg/ml) added simultaneously to PRP of control and treated rats. The results were assessed photometrically. Each test was replicated 4 times in groups of 3 animals. Aggregation curves were evaluated in terms of two parameters namely maximum optical density variation (maximum aggregation) and aggregation rate.

Table 4 gives the effects recorded after treatment with some of the tested compounds. They show an activity comparable to Ticlopidine and Suloctidil and only slightly lower than Dipiridamol.

TABLE 4

| Compound | % inhibition | |
|---|---|---|
| | Maximum aggregation | Aggregation rate |
| MG 38007 | 78.9 | 80.0 |
| MG 28414 | 54.0 | 58.0 |
| MG 28427 | 64.3 | 68.8 |
| Ticlopidine | 70.0 | 56.0 |
| Sulfinpyrazone | 92.5 | 89.0 |
| Suloctidil | 69.0 | 57.5 |

Sprague Dawley Nos male rats (180–200 g) were treated orally for 4 consecutive days with vehicle (0.5 ml/100 g gum arabic 2.5%, controls) and with 1–2 doses of the tested compounds, and were sacrificed at the 5th day after 18 hrs. fasting. Total cholesterol (CHOL), triglycerides (TG), HDL cholesterol CHOL-HDL) were assayed in serum and the liver was weighed.

Table 5 gives the obtained results. MG 38112 and MG 38107 cause a marked decrease both of CHOL and TG while MG 38041, MG 38128 and MG 38131 decrease TG and increase CHOL-HDL.

The liver weight is not affected. The effect of MG 38112 and MG 38107 is higher than with Clofibrate which, as known, causes a signicative liver increase, The Probucol activity is moderate and is noted only after prolonged treatment (8 days).

TABLE 5

| Compound | Dose mM/kg po | Normolipemic rats % difference from control | | | |
|---|---|---|---|---|---|
| | | CHOL | TG | CHOL-HDL | Liver weight |
| MG 38041 | 0.370 × 4 days | ~0 | −44.2 | +53.1 | +2.0 |
| MG 38112 | 0.185 × 4 days | −45.2 | −41.8 | −18.6 | 0 |
| MG 38112 | 0.370 × 4 days | −52.7 | −58.9 | −21.4 | +3.9 |
| MG 38107 | 0.185 × 4 days | −35.7 | −50.9 | −8.5 | +5.6 |
| MG 38107 | 0.370 × 4 days | −30.7 | −58.5 | −26.3 | 0 |
| MG 38128 | 0.370 × 4 days | ~0 | −38.8 | +46.8 | +8.6 |
| MG 36131 | 0.370 × 4 days | ~0 | −41.4 | +57.2 | +6.9 |
| Clofibrate | 0.820 × 4 days | −15.0 | −40.0 | 0 | +19.5 |
| Probucol | 0.205 × 8 days | −25.0 | −28.0 | −26 | +4 |
| Probucol | 0.820 × 4 days | ~0 | ~0 | +18.5 | ~0 |

The anti-hypoxic activity was determined according to Yasuda et al., Arch. Int. Pharmacodyn. 233, 136, 1978.

Groups of 10 male mice (21–23 g) were treated orally with vehicle (controls) and the invention compounds. After 45 or 90 minutes the animals were decapitated and the gasping time was determined. Table 6 gives the results obtained after administration of some of the invention compounds which display an activity higher than Suloctidil.

TABLE 6

| Compound | Dose mg/kg p.o. | Pretreatment time (min.) | Gasping time % diff. from control |
|---|---|---|---|
| MG 38404 | 100 | 45 | +31.0 |
| MG 38041 | 100 | 45 | +56.2 |
| MG 28400 | 100 | 45 | +53.8 |
| MG 38006 | 100 | 45 | +33.2 |
| MG 38100 | 100 | 45 | +95.7 |
| MG 16456 | 100 | 90 | +36.3 |
| Flunarizine | 50 | 90 | +68.7 |
| Suloctidil | 100 | 45 | +27.5 |
| Suloctidil | 100 | 90 | +11.7 |

The oral acute toxicity in male mice of the invention compound is very low. Thus, for example, the $LD_{50}$ is higher than 500 mg/kg for MG 38041, MG 28400 and MG 38100, higher than 1,000 mg/kg for MG 38019, MG 38006, MG 38112 and MG 38107; and higher than 2,000 mg/kg for MG 38005, MG 28401, MG 28414 and MG 28427.

EXAMPLE 1 cis and trans
2-[4-(2-Oxo-1-benzimidazolinyl)-1-piperidinil]-5,6-dimethoxy-1-indanol (MG 28401 and MG 28427).

A mixture of 3 g of 2-bromo-5,6-dimethoxy-1-indanone (Barltrop, J. Chem. Soc. 1946 958–965) (11 mmole), 2.17 g of 4-(2-oxo-1-benzimidazolinyl)-piperidine (10 mmole), 0.92 g of $NaHCO_3$ (11 mmole) in 60 ml of methanol is refluxed with stirring for 16 hours. The mixture is concentrated under reduced pressure, the residue is treated with ethyl acetate, the organic phase is washed with water, dried over sodium sulfate and evaporated under reduced pressure. Yield 3.1 g (76%) of 2-[4-(2-oxo-1-benzimidazolinyl)-1-piperidinyl]-5,6-dimethoxy-1-indanone, m.p. 240°–242° C. (dec.).

Analysis for $C_{23}H_{25}N_3O_4$% calc. C 67.79 H 6.18 N 10.31; found 67.65 6.17 10.29.

To 11.7 g (28.7 mmole) of the foregoing compound, dissolved in 600 ml of anhydrous tetrahydrofuran (THF), 2.18 g of $LiAlH_4$ (57 mmole) are added gradually with stirring at 20° C. under a nitrogen atmosphere, then the mixture is allowed to stand under stirring for 2 hours. After cooling to 0° C. the excess $LiAlH_4$ is treated with ethyl acetate and then with water.

The formed salts are filtered off and the solution is concentrated under reduced pressure. The obtained crude product is purified by flash chromatography through a column filled with silicagel 60 Merck 230–400 mesh and elution with a $CHCl_3$:$CH_3OH$ 95:5 mixture.

Yield 2.6 g (22%) of cis-isomer, m.p. 264°–266° C. after washing with hot ethanol-diethyl ether mixture; and 4.7 g (40%) of trans-isomer, m.p. 245°–247° C., after washing as above.

Analysis for $C_{23}H_{27}N_3O_4$ % calc. 67.45 H 6.64 N 10.26; cis-isomer found 67.31 6.63 10.24; trans-isomer 67.40 6.66 10.24.

The $^1H$ NMR analysis (300 MHz, Py d5) confirmed the cis resp. trans structure of the two isomers.

EXAMPLE 2 cis and trans
2-[4-(1-Oxo-3-phenyl-2-propenyl)-1-piperazinyl]-5,6-dimethoxy-1-indanol (MG 28404 and MG 28414).

A mixture of 3 g of 2-bromo-5,6-dimethoxy-1-indanone (11 mmole), 2.16 g of 1-cinnamoylpiperazine (10 mmole), 0.9 g of sodium bicarbonate (11 mmole) in 9 ml of methanol is refluxed with stirring for 16 hours. Then into the boiling mixture 0.77 g of $NaBH_4$ (20 mmole)

dissolved in 1.5 ml of water is dropped and the boiling temperature is maintained for another 4 hours.

The mixture is then cooled causing separation of a precipitate which is collected and washed with water.

On crystallization from ethanol 1.47 g of cis-isomer are obtained (yield 36%); m.p. 204°–206° C.

The filtered mother liquor from the reaction mixture is made acidic with aqueous 15% HCl and concentrated under reduced pressure. The residue is made alkaline by addition of an aqueous 5% sodium carbonate solution and extracted with methylene dichloride.

The organic phase is washed with water until neutral and dried over sodium sulfate. The residue which is obtained by evaporation of the solvent under reduced pressure is crystallized from acetone. 1.22 g of trans-isomer are obtained (yield 30%); m.p. 168°–170° C.

Analysis for $C_{24}H_{28}N_2O_4$ % calc. C 70.48 H 6.90 N 6.85; cis-isomer found 70.34 6.89 6.83; trans-isomer 70.40 6.86 6.80.

EXAMPLE 3 trans 5,6-Dimethoxy-2-(n-octylamino)-1-indanol (MG 28400)

To a mixture of 2.5 g of 2-amino-5,6-dimethoxy-1-indanol hydrochloride (10.2 mmole) (R. Perrone et al., il Farmaco, Ed. Sci., 39, 255–264, 1984), 1.44 g of octanal (11.2 mmole) and 100 ml of methanol, 2.5 g of sodium cyanoborohydride (39.8 mmole) is added gradually with stirring at 5° C. The mixture is then allowed to stand at room temperature overnight with stirring, then the mixture is made acidic by the addition of dilute HCl while cooling at 5° C., then sodium bicarbonate is added to alkaline reaction and the mixture is extracted with chloroform. The organic phase is dried over sodium sulfate and concentrated under reduced pressure. The crude residue is purified by crystallization from acetone/hexane. Yield 1.5 g (45.7%); m.p. 133°–135° C.

Analysis for $C_{11}H_{16}ClNO_3$ % calc. C 53.77 H 6.56 N 5.70; found 53.61 6.54 5.68.

EXAMPLE 4 cis and trans 2-[4-(1-Oxo-3-phenyl-2-propenyl)-1-piperazinyl]-4,5,6-trimethoxy-1-indanol (MG 38004 and MG 38015).

A mixture of 3.3 g (11 mmole) of 2-bromo-4,5,6-trimethoxy-1-indanone (Haworth et al., J. Chem. Soc. 1952 1583–1588), 2.16 g (10 mmole) of 1-(1-oxo-3-phenyl-2-propenyl)-piperazine, 0.92 g (11 mmole) of $NaHCO_3$ in 8 ml of methanol is refluxed with stirring for 16 hours. After cooling, and maintaining the temperature at 0°–5° C., 0.77 g (20 mmole) of $NaBH_4$ are added at portions, then the mixture is allowed to stand for 4 hours at room temperature under stirring. The mixture is cooled and made acidic by the addition of 15% aqueous HCl. After concentration under reduced pressure, the mixture is made alkaline by the addition of an aqueous 5% solution of sodium carbonate and extracted with methylene dichloride. The organic phase is washed with $H_2O$ to neutrality and dried over sodium sulfate. On evaporation under reduced pressure, 4.2 g are obtained as a mixture of diastereoisomers cis/trans which are separated by flash-chromatography through a column filled with silicagel 60 Merck 230–400 mesh, using chloroform:acetone 50:50 as the eluent. After crystallization from acetone, 1,2 g of cis-isomer are obtained (yield 27.4%), m.p. 162–163° C. On cristallization from acetone, 1.25 g of trans-isomer are obtained (yield 28.5%); m.p. 168°–170° C.

Analysis for $C_{25}H_{30}N_2O_5$ % calc. C 68.47 H 6.89 N 6.39; cis-isomer found 68.33 6.88 6.40; trans-isomer 68.40 6.86 6.40.

EXAMPLE 5 cis and trans 2-[4-(2-Oxo-2-benzimidazolinyl)-1-piperidinyl]-4,5,6-trimethoxy-1-indanol (MG38007 and MG 38019)

A mixture of 3.3 g of 2-bromo-4,5,6-trimethoxy-1-indanone (11 mmole), 2.17 g of 4-(2-oxo-1-benzimidazolinyl)-piperidine (10 mmole), 0.92 g of $NaHCO_3$ (11 mmole) in 60 ml of methanol is refluxed under stirring for 5 hours, the mixture is then cooled and the precipitate is collected and washed with water, then with methanol for 30 minutes at 40° C.

Yield 3 g (68.5% of 2-[4-(2-oxo-1-benzimidazolinyl)-1-piperidinyl]-4,5,6-trimethoxy-1-indanone, m.p. 197°–199° C. (MG 38005).

Analysis for $C_{24}H_{27}N_3O_5$ % calc. C 65.88 H 6.22 N 9.60; found 65.68 6.20 9.57.

To 2 g (4.6 mmole) of the foregoing intermediate in 10 ml of methanol, 0.35 g of $NaBH_4$ (9.2 mmole) dissolved in 1 ml of water is dropped with stirring at the boiling temperature of the solvent. Heating is then continued for additional 3 hours.

After cooling the reaction mixture is made acidic by the addition of aqueous 15% HCl, then it is concentrated under reduced pressure, the residue is treated with aqueous 5% $Na_2CO_3$ solution to alkaline reaction and extracted with $CH_2Cl_2$. The organic phase is washed with water and dried over sodium sulfate. On evaporation under reduced pressure a mixture of cis-trans diastereoisomers is obtained which are separated by flash chromatography using $CHCl_3:CH_3OH$ 95:5 as the eluent. After crystallization from aqueous methanol 1.38 g of cis-isomer (yield 68.2%) are obtained; m.p. 238°–239° C. By washing with hot acetone, 0.44 g (yield 21.8%) of trans-isomer are obtained; m.p. 256°–258° C.

Analysis for $C_{24}H_{28}N_3O_5$ % calc. C 65.58 H 6.65 N 9.56; cis-isomer found 65.45 6.64 9.54; trans-isomer 65.48 6.60 9.52.

EXAMPLE 6 trans 2-(n-Octylamino)-4,5,6-trimethoxy-1-indanol (MG 38006)

Into 16 g of 4,5,6-trimethoxy-1-indanone (Haworth et al., J. Chem. Soc. 1952 1583–88) in 280 ml of anhydrous diethyl ether at the temperature of 15°–20° C. and with stirring, anhydrous hydrogen chloride is bubbled while simultaneously dropping into the solution 9 ml of n-butyl nitrite. When the n-butyl nitrite addition is terminated, bubbling of HCl is continued at 5° C. until precipitation is complete. The precipitate is collected and washed with diethyl ether and crystallized from ethanol. Yield 13.4 g (74%) of 2-isonitroso-4,5,6-trimethoxy-1-indanone; m.p. 203°–204° C.

To a solution of 2 g of the foregoing compound in 20 ml of methanol, 4 ml of a 20% solution of HCl in ethanol are added; then the mixture is hydrogenated in the presence of 0.5 g of 5% Pd/C at room temperature and pressure. The catalyst is then filtered off and the solution is concentrated under reduced pressure. the residue is recrystallized from methanol/diethyl ether giving 1.66 g (yield 76.2%) of 2-amino-4,5,6-trimethoxy-1-indanone hydrochloride; m.p. 206°–208° C. (dec.)

The above obtained amino ketone hydrochloride is dissolved in 50 ml of methanol, then 2 g of NaBH₄ are added in small portions at 5° C. under continuous stirring. the mixture is then allowed to stand at room temperature for 1 hour, then it is diluted with water, extracted with chloroform and the organic solution is dried over magnesium sulfate. After concentration under reduced pressure the residue is cristallized from chloroform/hexane. The product is dissolved in methanol and treated with HCl in ethanol giving 1.09 g of trans-2-amino-4,5,6-trimethoxy-1-indanol hydrochloride on addition of diethyl ether, as a precipitate having m.p. 167° C. (dec.); yield 54%. To a mixture of 4 g of the above obtained hydrochloride, 2.06 g of octanal and 150 ml of $CH_3OH$, 4.1 g of $NaBH_3CN$ are gradually added at 5° C. with stirring, then the mixture is allowed to stand overnight at room temperature. After this time it is cooled to 5° C., made acidic with 15% HCl, diluted with water, then made alkaline with sodium bicarbonate, extracted with chloroform and the organic extract is dried over sodium sulfate and concentrated to dryness under reduced pressure.

The crude product is purified by flash chromatography, eluent $CHCl_3:CH_3OH$ 95:5. By crystallization from acetone/hexane, 2 g of product are obtained (yield 39%), m.p. 123°–124° C.

Analysis for $C_{20}H_{33}NO_4$ % calc. C 68.34 H 9.46 N 3.98; found 68.20 9.44 3.97.

EXAMPLE 7 cis and trans 2-[4-(1-Oxo-3-phenyl-2-propenyl)-1-piperazinyl]-6,7-dimethoxy-1-tetralol (MG 38056 and MG 38035).

A mixture of 2.76 g of 2-bromo-6,7-dimethoxy-1-tetralone (Wilds., J. Am. Chem. Soc. 64 1421, 1942), 1.9 g of cinnamoylpiperazine and 0.81 g of sodium bicarbonate in 20 ml of methanol is refluxed with stirring for 6 hours. Still at the boiling temperature, 0.66 g of NaBH₄ dissolved in 3 ml of water are dropped and reflux is continued for additional 6 hours.

The mixture is then cooled, diluted with water and extracted with chloroform. From the organic extract a mixture of cis-trans diastereoisomers is obtained by evaporation of the solvent; they are separated by flash chromatography using chloroform:acetone 70:30 as the eluent. After crystallization from aqueous ethanol, 0.97 g (26.1%) of trans-isomer, m.p. 168°–170° C., and 0.94 g (25.3%) of cis-isomer, m.p. 102°–104° C., are obtained.

Analysis for $C_{25}H_{30}N_2O_4$ % calc. C 71.06 H 7.15 N 6.63; cis-isomer found 70.92 7.13 6.62; trans-isomer 71.01 7.12 6.65.

The coupling constant was determined by ¹H NMR (300 MHz) in pyridine. For the trans-isomer it was $J_{1,2}=9.7$ Hz; [for the cis-isomer it was $J_{1,2}=3,5$ Hz].

EXAMPLE 8 cis- and trans 2-[4-(2-Oxo-1-benzimidazolinyl)-1-piperidinyl]-6,7-dimethoxy-1-tetralol (MG 38060 and MG 38041).

A mixture of 3 g of 2-bromo-6,7-dimethoxy-1-tetralone, 2.28 g of 4-(2-oxo-1-benzimidazolinyl)-piperidine and 0.9 g of NaHCO₃ in 60 ml of methyl ethyl ketone is heated at 60° C. with stirring for 7 hours under a nitrogen atmosphere, then stirring is continued overnight at room temperature. The mixture is cooled to 0° C. and the precipitate is collected and washed with diethyl ether. Yield 4.2 g (94.9%, m.p. 238°–239° C.) of 2-[4-(2-oxo-1-benzimidazolinyl)-1-piperidinyl]-6,7-dimethoxy-1-tetralone which is used as such for the following step.

To 2.95 g of the foregoing compound dissolved in 40 ml of tetrahydrofuran (THF), 0.53 g of LiAlH₄ are gradually added under a nitrogen atmosphere. Stirring is then continued for additional 3 hours at room temperature, then the mixture is cooled and the excess hydride is destroyed with et hyl acetate and with ice. The mixture is filtered and the filtrate is concentrated under reduced pressure. The residue is treated with chloroform, washed with water and evaporated to dryness. The distereoisomeric mixture is separated by flash chromatography using $CHCl_3:CH_3OH$ 95:5 as the eluent.

trans-isomer: yield 1.2 g (40.5%), m.p. 206°–208° C.
cis-isomer: yield 0.4 g (13.5%), m.p. 233°–235° C.

The configuration was determined by ¹H NMR (300 MHz) in CDCl₃. The coupling constant was $J_{1,2}=9.7$ Hz for the trans-isomer and $J_{1,2}=2.5$ Hz for the cis-isomer.

Analysis for $C_{24}H_{29}N_3O_4$ calc. % C 68.05 H 6.80 N 9.92; cis-isomer 67.91 6.89 9.90; trans-isomer 66.92 6.88 9.91.

The following is a complete reporte of the NMR obtained.

TRANS

δH: 10.15 (1H, br, NH); 7.30–7.00 (4H, m,

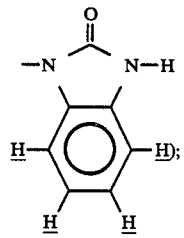

7.13 (1H, s,

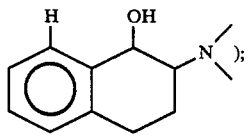

6.57 (1H, s,

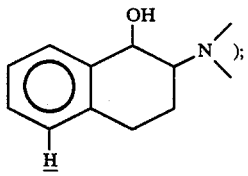

4.66 (1H, d, J=9.7 Hz,

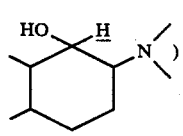

4.40 (1H, m, piperidinic); 3.91 and 3.86 (2×3H, s, OMe) 3.13 (1H, m, piperidinic); 2.91 (2H, m, piperidinic) 2.91 (2H, m,

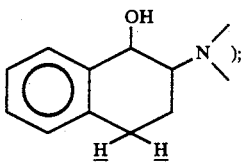

2.72 (1H, m,

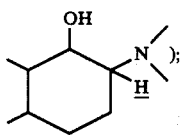

2.65–2.20 (3H, m piperidinic); 2.10 and 1.66 (2×1H, m,

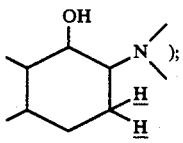

1.94 (2H, m, piperidinic).

CIS

δH: 9.76 (1H, br, NH); 7.30–7.00 (4H, m,

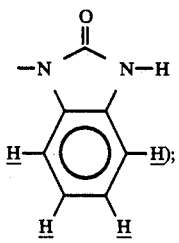

6.93 (1H, s,

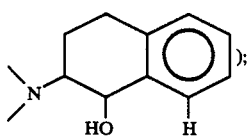

6.62 (1H, s,

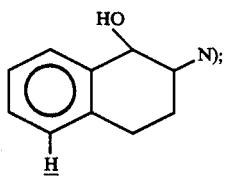

4.77 (1H, d,

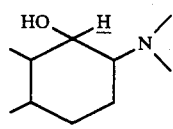

J=2.5 Hz); 4.44 (1H, m, piperidinic) 3.89 and 3.87 (2×3H, s, OMe); 3.50 and 3.36 (2×1H, m, piperidinic) 3.00–2.50 (6H, m, 4H piperidinic +2H

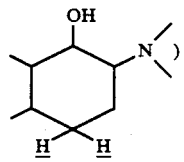

2.10–1.80 (4H, m, 2H piperidinic +2H

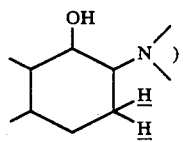

EXAMPLE 9 cis and trans 2-[4-(1-Oxo-3-phenyl-2-propenyl)-1-piperazinyl]-5,6,7-trimethoxy-1-tetralol (MG 38033 and MG 38025).

To a solution of 3.54 g of 5,6,7-trimethoxy-1-tetralone (Snider et al., Organic Preparations and Procedures Int., 5 (6) 291–298, 1973) in 40 ml of THF under stirring and at room temperature, 5.64 g of phenyl trimehyl ammonium tribromide is gradually added in a period of 6 hours, then stirring is continued for additional 30 minutes, after which the mixture is poured into 400 ml of a 5% NaHCO$_3$ solution and ice, and extracted with diethyl ether. From the organic phase a residue is obtained by evaporation and is crystallized from ethanol.

Yield 4.09 g (86.5%) of 2-bromo-5,6,7-trimethoxy-1-tetralone, m.p. 107°–107.5° C. This intermediate compound is used for the preparation of the title compounds by substantially the same process as described in Example 7 for the 6,7-dimethoxy analogue. Purification was effected by crystallization from acetone/hexane.

cis-isomer: yield 1.45 g (32%), m.p. 171°–172° C.,
trans-isomer: yield 0.95 g (21%) m.p. 140°–142° C.,
Analysis for $C_{26}H_{32}N_2O_5$ % calc. C 69.9 H 7.13 N 6.19; cis-isomer found 68.86 7.11 6.18; trans-isomer 68.91 7.15 6.19.

The configuration was determined by $^1$H NMR (300 MHz) in CDCl$_3$. The coupling constant was $J_{1,2}=10.23$ Hz for the trans-isomer and 3.5 Hz for the cis-isomer.

EXAMPLE 10 trans 2-[4-(2-Oxo-1-benzimidazolidinilyl)-1-piperidinyl]-5,6,7-trimethoxy-1-tetralol (MG 38028).

By substantially the same process as described in the first part of Example 8 for the 6,7-dimethoxy analogue, the intermediate 2-[4-(2-oxo-1-benzimidazolinyl)-1-piperidinyl]-5,6,7-trimethoxy-1-tetralone was prepared in a 70% yield and showed m.p. 215° C. (dec.). To 5 g of this intermediate dissolved in 100 ml of THF, 1.23 g of LiAlH$_4$ is gradually added under stirring under a nitrogen atmosphere at 10° C., then stirring is continued at room temperature for 5 hours.

After cooling to 0° C. the excess hydride is destroyed with ethyl acetate and then with water and the mixture is filtered.

The filtrate is evaporated to dryness under reduced pressure, the residue is dissolved in chloroform and the solvent removed in vacuo. By column chromatography and elution with chloroform:acetone 60:40, the trans-isomer is obtained, m.p. 237°–239° C., yield 2.5 g (49.8%).

Analysis for C$_{25}$H$_{31}$N$_3$O$_5$ % calc. C 66.20 H 6.89 N 9.26; found 66.07 6.88 9.24.

The configuration was determined by $^1$H NMR (300 MHz) in pyridine. The coupling constant was J=10.23 Hz.

By procedures substantially identical to those described in the preceding disclosure and Examples the following compounds were prepared. Yields of final step and melting points are given.

EXAMPLE 11 cis- and trans-2-[4-(2-Oxo-5-chloro-1-benzimidazolinyl)-1-piperidinyl]-4,5,6-trimethoxy-1-indanol.

Prepared from 2-bromo-4,5,6-trimethoxy-1-indanone and 4-(2-oxo-5-chloro-1-benzimidazolinyl)-piperidine in the presence of NaHCO$_3$ and hydrogenation of the intermediate with NaBH$_4$. The diastereomeric mixture was separated by flash chromatography through silica gel and elution with CHCl$_3$:CH$_3$OH 95:5 mixture.

cis (MG 38119): 39.8%; 242°–244° C. (dec.)
trans (MG 38122): 13.3%; 244°–246° C. (dec.)

EXAMPLE 12 cis and trans-2-[4-(2-Oxo-5-chloro-1-benzimidazolinyl)-1-piperidinyl]-5,6-dimethoxy-1-indanol.

Prepared from 4-(2-oxo-5-chloro-1-benzimidazolinyl)-piperidine and 2-bromo-5,6-dimethoxy-1-indanone as described in the foregoing example. The intermediate ketone 2-[4-(2-oxo-5-chloro-1-benzimidazolinyl)-1-piperidinyl]-5,6-dimethoxy-1-indanone (MG 38120) was obtained in 70.1% yield and has m.p. 250°–254° C. (dec).

By hydrogenation with NaBH$_4$ the only cis form was isolated in 47.8% yield. Using LiAlH$_4$ as the hydrogenating agent a mixture of the cis and trans forms is obtained and is separated by chromatography through silica gel. Yields were 27.9% of cis and 37.8% of trans form.

cis (MG 38121): 279°–281° C. (dec.)
trans (MG 38131): 259°–261° C. (dec.)

EXAMPLE 13 cis and trans 2-(4-Benzamido-1-piperidinyl)-5,6-dimethoxy-1-indanol.

Prepared from 4-benzamidopiperidine and 2-bromo-5,6-dimethoxy-1-indanone. The intermediate 2-(4-benzamido-1-piperidinyl-5,6-dimethoxy-1-indanone (MG 38128) was obtained in 65.8% yield and showed m.p. 238°–240° C. (dec.). Hydrogenation is carried out with NaBH$_4$.

cis (MG 38112): 46.6%; 243°–244° C. (methanol)
trans (MG 38130): 9.1%; 235°–236° C. (dec.)

EXAMPLE 14 cis-2-[4-(2-Methyl-1-benzimidazolinyl)-piperidinyl]-5,6-dimethoxy-1-indanol (MG 38125).

Prepared from 4-(2-methyl-1-benzimidazolinyl)-piperidine hydrochloride hydrobromide and 2-bromo-5,6-dimethoxy-1-indanone without isolation of the intermediate ketone and using NaBH$_4$ as the hydrogenating agent. Yield 54.7%; m.p. 255°–256° C. (chloroform/diethyl ether).

By procedures analogous to those of the foregoing examples the following compounds were prepared starting from the appropriate intermediates.

EXAMPLE 15 cis-2-(4-Benzamido-1-piperidinyl)-4,5,6-trimethoxy-1-indanol (MG 38107): 62.3%; 197.5°–198.5° C.

EXAMPLE 16 cis-2-[4-(2-Methoxyphenyl)-1-piperazinyl]-5,6-dimethoxy-1-indanol (MG 38100): 44,7%; m.p. 192°–194° C.

EXAMPLE 17 trans-2-[4-(2-Methoxyphenyl)-1-piperazinyl]-4,5,6-trimethoxy-1-indanol (MG 38099): 29.8%; 167°–168° C. (ethanol).

EXAMPLE 18

2-[4-(2-Methyl-1-benzimidazolinyl)-1-piperidinyl]-4,5,6-trimethoxy-1-indanol.

cis (MG 38129); 42.8%; 198°–200° C. (isopropanol)
trans (MG 38133); 17.2% 151°–153° C. (ethanol).

EXAMPLE 19 cis and trans-2-[4(2-Oxo-5-chloro-1-benzimidazolinyl)-1-piperidinyl]-5,6,7-trimethoxy-1-tetralol.

cis (MG 16489) 10%; 124°–126° C. (CHCl$_3$/petroleum ether)
trans (MG 16456) 40%; 222°–224° C. (isopropanol)

The intermediate ketone, 2-[4-(2-oxo-5-chloro-1-benzimidazolinyl)-1-piperidinyl]-5,6,7-trimethoxy-1-tetralone (MG 16459) showed m.p. 205°–209° C. (methyl ethyl ketone).

EXAMPLE 20

2-[4-(2-Oxo-1-benzimidazolinyl)-1-piperilidenyl]-4,5,6-trimethoxy-1-indanone (MG 38114): 25.3%, 174°–177° C. (dec.).

EXAMPLE 21 cis-2-[4-(2-Oxo-1-benzimidazolinyl)-methyl-1-piperidinyl]-4,5,6-trimethoxy-1-indanol (MG 38142): 30.3%, 224°–226° C. (ethanol).

EXAMPLE 22

2-[4-(2-Oxo-1-benzimidazolinyl)-1-piperilidienyl]-5,6-dimethoxy-1-indanone (MG 38136): 47.3%; 224°–226° C. (DMF/H$_2$O).

EXAMPLE 23 cis-2-[4-(2-Oxo-1-benzimidazolinyl)-methyl-1-piperidinyl]-5,6-dimethoxy-1-indanol (MG 38140): 47.4%; 236°–238° C. (CHCl₃/ethyl ether).

EXAMPLE 24

2-[4-(2-Methyl-1-benzimidazolinyl)-1-piperidinyl]-5,6,7-trimethoxy-1-tetralol.

cis (MG 16490): 15%; 100°–104° C. (dec.)
trans (MG 16478): 26%; 100°–105° C. (dec.)
The NMR spectra confirm the structure.

EXAMPLE 25 trans-2-(4-Benzamido-1-piperidinyl)-5,6,7-trimethoxy-1-tretralol (MG 16480): 15%; 190°–192° C.

We claim:

1. A compound of the formula:

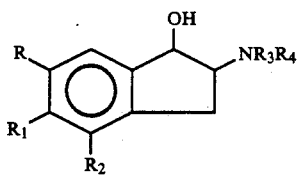

in its cis and trans configurations and mixtures thereof, wherein R,

R₁ and R₂ each represent hydrogen or a lower alkoxy group, with the proviso that at least two alkoxy groups are present; or adjacent pairs of radicals of the combinations of R+R₁ and R₁+R₂ represent an alkylenedioxy group;

R₃ and R₄ taken together represent a divalent group selected from the group consisting of:

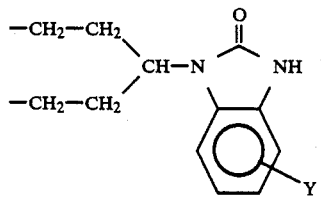 (a)

wherein Y represents hydrogen or halogen;

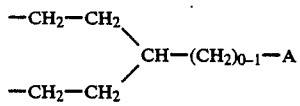 (b)

wherein A is a group selected from the group consisting of:

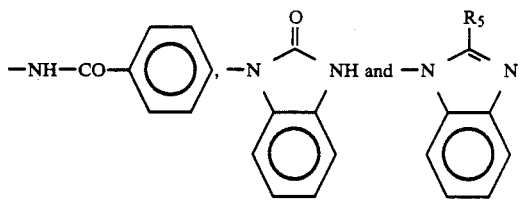

wherein R₅ represents a lower alkyl group;

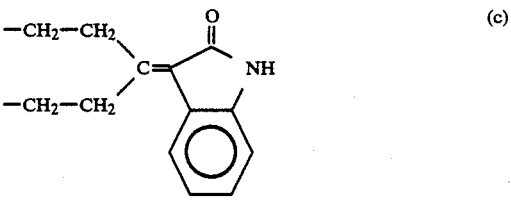 (c)

and

 (d)

wherein W represents hydrogen, phenyl, alkoxyphenyl, 2-furoyl, nicotinoyl or the radical:

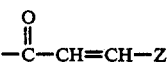

in which Z represents 2-thienyl or phenyl, optionally substituted with 1–3 halogen or alkoxy groups; and its salts with inorganic and organic acids.

2. A compound selected from the racemate and the cis and the trans stereoisomeric forms of 2-[4-(2-oxo-1-benzimidazolinyl)-1-piperidinyl]-5,6-dimethoxy-1-indanol.

3. A compound selected from the racemate and the cis and trans stereoisomeric forms of 2-[4-(2-oxo-1-benzimidazolinyl)-1-piperidinyl]-4,5,6-trimethoxy-1-indanol.

4. A compound selected from the racemate and the cis and the trans stereoisomeric forms of 2-[4-(1-oxo-3-phenyl-2-propenyl)-1-piperazinyl]-5,6-dimethoxy-1-indanol.

5. A compound selected from the racemate and the cis and the trans stereoisomeric forms of 2-(4-benzamido-1-piperidinyl)-5,6-dimethoxy-1-indanol.

6. A compound selected from the racemate and the cis and the trans stereoisomeric forms of 2-(4-benzamido-1-piperidinyl)-4,5,6-trimethoxy-1-indanol.

7. A compound selected from the racemate and the cis and the trans stereoisomeric forms of 2-[4-(2-oxo-5-chloro-1-benzimidazolinyl)-1-piperidinyl]-5,6-dimethoxy-1-indanol.

* * * * *